United States Patent
Derakhshan (12)

(10) Patent No.: US 6,333,352 B1
(45) Date of Patent: Dec. 25, 2001

(54) METHOD OF TREATING BENIGN POSITIONAL VERTIGO

(75) Inventor: Iraj Derakhshan, Charleston, WV (US)

(73) Assignee: Mimicking Man Manually, Inc., Charleston, WV (US)

( * ) Notice: Subject to any disclaimer, the term of this patent is extended or adjusted under 35 U.S.C. 154(b) by 0 days.

(21) Appl. No.: 09/543,746

(22) Filed: Apr. 5, 2000

(51) Int. Cl.$^7$ .................. A61K 31/19; A61K 31/215
(52) U.S. Cl. ............................ 514/557; 514/530
(58) Field of Search ...................... 514/557, 530

(56) References Cited

U.S. PATENT DOCUMENTS

| | | | |
|---|---|---|---|
| 4,466,438 | 8/1984 | Katz | 128/400 |
| 4,894,476 | 1/1990 | Butler et al. | 562/504 |
| 4,960,931 | 10/1990 | Butler et al. | 562/507 |

OTHER PUBLICATIONS

Todd et al. "Flunarizine. A reappraisal of its pharmacological properties and therapeutic use in neurological disorders." Durgs, (Oct. 1989) 38(4) 481–99. Ref: 124 Journal code: EC2. ISSN: 0012-6667.*

Fisher et al. "Clobazem, oxcarbazepine, tiagabine, topiramate, and other new antiepileptic drugs." Epilepsia (N.Y.) (1995), 36(Suppl. 2), S105–S114 Coden: EPILAK; ISSN: 0013-9580.*

Neurontin, Product description from manufacturer, Parke Davis Pharmaceuticals, Ltd., 1998.

Depakote Tablets, Product description from manufacturer, Abbott Laboratories, Aug., 1999.

Davies, "Mechanism of action of antiepileptic drugs", British Epilepsy Association, Seizure, pp. 267–272, 1995.

Macdonald et al., "Antiepileptic Drug Mechanisms of Action", Epilepsia 36(Suppl. 2), pp. S2–S12, 1995.

Radulovic et al., "Lack of Interaction of Gabapentin with Carbamazepine or Valproate", Epilepsia, 35(1) pp. 155–161, 1994.

Macdonald et al., "Mechanisms of Action of Currently Prescribed and Newly Developed Antiepileptic Drugs", Epilepsia, 35(Suppl. 4) pp. S41–S50, 1994.

* cited by examiner

Primary Examiner—Theodore J. Criares
Assistant Examiner—Jennifer Kim
(74) Attorney, Agent, or Firm—Heller Ehrman White & McAuliffe LLP

(57) ABSTRACT

A process and product for treating benign positional vertigo with anti-epileptic drugs such as divalproex sodium or gabapentin.

17 Claims, No Drawings

METHOD OF TREATING BENIGN POSITIONAL VERTIGO

FIELD OF THE INVENTION

This invention relates to the field of treating vertigo, especially benign positional vertigo.

BACKGROUND OF THE INVENTION

Benign positional vertigo (BPV) is the most common cause of pathological vertigo. The cause of about half of the cases of BPV is unknown, particularly in the elderly, while the remaining cases are linked to causes such as head injury, vascular occlusion and viral labyrinthitis. Patients suffering from BPV develop brief episodes of vertigo. This particularly occurs while the patient is changing position in such tasks as bending over and standing up, extending the neck to acquire a more elevated view, getting in and out of bed, and turning over in bed. In most patients the symptoms spontaneously remit, but recurrence is frequent.

A possible cause of BPV is thought to be free-floating calcium carbonate crystals, normally attached to the utricular macule, which accidently enter the long arm of the posterior semicircular canal. One therapy for alleviating the symptoms of BPV has been a bedside positioning maneuver used to remove the debris from the posterior canal on the affected side. This manipulation of the head; however, does not cure all symptoms and requires the patient to visit the office of a medical practitioner capable of performing such a manipulation. BPV has also be treated with the administration of meclazine; however, few patients respond to meclazine.

SUMMARY OF THE INVENTION

In accordance with the present invention, the inventor has unexpectedly found that anti-epileptic drugs can be used to treat benign positional vertigo and symptoms of benign positional vertigo. For example, gabapentin or a salt of divalproex, such as divalproex sodium have been successfully used to treat benign positional vertigo. These two drugs have not been previously known for efficacy in treating benign positional vertigo. The invention also contemplates using anti-epileptic drugs, such as divalproex sodium or gabapentin for a prophylaxis treatment of migraine headaches which are at times associated with BPV.

In one embodiment of the present invention, a salt of divalproex, such as sodium divalproex, is administered in a pharmaceutically effective amount to a patient suffering from benign positional vertigo. Divalproex sodium is a coordination compound of sodium valproate and valproic acid in a 1:1 molar ratio and is chemically designated as sodium bis(2-propylpentanoate).

In another embodiment of the present invention, gabapentin is administered in a pharmaceutically effective amount to a patient suffering from benign positional vertigo. Gabapentin is chemically designated as 1-(aminomethyl) cyclohexaneacetic acid.

Additional features and advantages of the invention will be set forth in the description which follows, and in part will be obvious from the description, or may be learned by practice of the invention.

DETAILED DESCRIPTION OF THE INVENTION

The present invention involves administering an anti-epileptic drug to a patient suffering from BPV in a pharmaceutically acceptable amount. Examples of such anti-epileptic drugs include gabapentin or a salt of divalproex, such as divalproex sodium. Gabapentin is offered by Parke-Davis under the trademark Neurontin® in hard shell capsules containing 100 mg, 300 mg, and 400 mg of gabapentin. The inactive ingredients include lactose, cornstarch, talc, gelatin, and titanium dioxide. Divalproex sodium is a stable coordinated compound of sodium valproate and valproic acid in a 1:1 molar ratio and is formed during the partial neutralization of valproic acid with 0.5 equivalent of sodium hydroxide. Divalproex sodium is sold by Abbott Laboratories under the trademark Depakote® in tablets with dosage strengths containing divalproex sodium equivalent to 125 mg, 250 mg, or 500 mg of valproic acid. The inactive ingredients include cellulosic polymers, diacetylated monoglycerides, povidone, pregelatinized starch, silica gel, talc, titanium oxide and vanillin.

The inventor has also observed that the following relationship is often true in the diagnosis of BPV and subsequent treatment with Neurontin® or Depakote®. Symptoms of BPV include vertigo when changing position in such tasks as bending over and standing up, extending the neck to acquire a more elevated view, getting in and out of bed, turning over in bed looking up, bending over, looking down, getting up, and lying down. When symptoms of BPV have occurred in relationship to a virus, such as vestibular neuronitis, several weeks of treatment are needed to eliminate or reduce the BPV symptoms. If BPV manifests itself in relationship to a head trauma, two to three months of treatment are generally required. When symptoms of BPV are ediopathic (unknown), several months to an indefinite time may be required to control the symptoms of BPV. When patients do not respond to either medication, this is often because the cause of the positional vertigo is due to a structural lesion.

Neurontin® or Depakote® can be prescribed at any dosage that is effective in relieving symptoms of BPV or BPV associated with a migraine headache. The inventor has found an effective dosage range of Depakote® to be 250 to 1,000 mg taken twice a day. Neurontin® has found to be effective in the dosage range of 400 to 1,200 mg taken twice a day. The following are actual patient histories of individuals treated with Neurontin® or Depakote®. In most patients the following symptoms of BPV were reduced within a week and did not reoccur after a few weeks or months of treatment. Treatment for most patients was discontinued after a few months. It has also been discovered that symptoms of BPV associated with migraine headaches can be effectively treated with the use of Neurontin® or Depakote®. Either drug can act as a prophylaxis in preventing the onset of migraine headaches.

EXAMPLE 1

Subject had undergone extensive evaluation for the complaint of staggering, which was of gradual onset. She had a spell of the same which was associated with clamminess and nausea as well as spinning of the environment for 20 minutes, not associated with headaches. Similar episodes had occurred a year previous without headache but again with nausea. The past history was remarkable for bad headaches when she was 18 years of age and none since. She had 6 children, with 3 sons suffering from headaches. Another aspect of the past history was occasional occurrences of dizziness when she suddenly stands up or looks up. Subject was diagnosed with benign positional vertigo and prescribed 300 mg of Neurontin® three times a day. Episodes of dizziness and staggering were substantially reduced.

EXAMPLE 2

Subject had dizzy spells that began after a big rock fell on his body, measuring 3 feet long, 3 feet wide and 4 inches in depth, hitting him in the left occiput and dorsal spine, but not knocking him out completely. Sine then he has had these dizziness episodes. Subject apparently fractured the dorsal vertebra 5, 7, and 11 and lacerated his liver in the process, sustained a fracture of the right leg and required surgery on the same. He complained of episodic occurrences of the spinning of the environment associated with sweating and of back ache and pain in the legs. Subject denied any headaches. Subject was diagnosed with benign positional vertigo and prescribed 400 mg of Neurontin® two times a day. Dizziness episodes disappeared after several days.

EXAMPLE 3

Subject had complained of dizziness and vomiting during the previous week. She got dizzy when she laid down and when she got up. Subject associated with dizziness with a headache that was interrupted as a "regular migraine," which she usually had for a day around time of her period. Two days later she had sudden onset of vertigo, positional, associated with vomiting and blurred vision. Subject was diagnosed with benign positional vertigo and prescribed 300 mg of Neurontin® two times a day. Both dizziness episodes and migraine headache disappeared after several days. After a few months of treatment, episodes of BPV did not reoccur.

EXAMPLE 4

Subject complained of benign positional vertigo, which had woke him up and eventually brought him to the hospital. This was in the form of the room turning around and was associated with some nausea. Similar events occurred six years ago and improved without treatment. Subject was diagnosed with benign positional vertigo and prescribed two 500 mg doses of Neurontin® at night and one 500 mg dose in the morning. The large dose at night was to aid subject in sleeping. Symptoms of BPV were reduced within a few days a subsequently disappeared within a few weeks.

EXAMPLE 5

Subject had a MI (myocardial insufficiency), onset with sudden chest pain. Following this she developed pancreatitis and underwent a cholecystectomy. The pancreatitis was due to a gallstone. Subsequently, subject complained of dizziness when she bends over and staggering remains when she walks. Subject was diagnosed as having BPV and prescribed Depakote® 500 twice a day. Symptoms of BPV were reduced within two weeks and did not reoccur after a few months of treatment.

EXAMPLE 6

Subject's main complaint was dizzy spells occurring over the past ten years associated with a falling to the left side and difficulty walking, profuse sweating and with the absence of headaches. He also complains of a continuous noise in the ear for the past two years, roaring in quality. Subject was originally diagnosed with Meniere's disease and placed on a low sodium diet that stopped these symptoms for rare occasions, only to restart in again. Symptoms continued on unabated even though subject as on a low sodium diet. The buzzing has since been continuous and subject lost his hearing on the left side by 75%. There is no family history of the same and no headache at all. Whenever subject lowered his head in preparation for swing at a golf ball, a dizzy spell would occur. The last attack before diagnosis occurred on the morning of the visit, at 5:00 am when woke up to go to the bathroom. He felt good and when he came back and lied down, he turned his head to the left, he began to sweat, was feeling dizzy and felt hot. Symptoms lasted for an hour. This wasn't associated with nausea but he felt that his scalp was tightening. There was no sense of rotation of the environment, on this occasion, but he used to have violent episodes before. Subject was diagnosed as having BPV and prescribed Depakote® 500 twice a day. Symptoms of BPV were reduced within a week and did not reoccur after a few months of treatment.

EXAMPLE 7

Subject complained of "dizzy spells". When she gets up or lays down the room goes round and round and this has been present for the past 2 to 3 months. Subject was diagnosed as having BPV and was prescribed Depakote® 500 twice a day. Symptoms of BPV subsequently disappeared in the subject.

Additional advantages, features and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents. As used herein and in the following claims, articles such as "the", "a" and "an" can connote the singular or plural.

I claim:

1. A method of treating a patient with symptoms of benign positional vertigo, comprising: administering a pharmaceutically effective amount of a pharmaceutically acceptable salt of divalproex or gabapentin.

2. A method for treating a patient with symptoms of benign positional vertigo, comprising: administering a pharmaceutically effective amount of a pharmaceutically acceptable salt of divalproex.

3. A method of claim 2, wherein said salt of divalproex is sodium.

4. A method of claim 2, wherein said pharmaceutically acceptable salt of divalproex is administered orally.

5. A method of claim 2, wherein said amount is from about 250 to about 1,000 mg taken twice per day.

6. A method for treating a patient with symptoms of benign positional vertigo, comprising: administering a pharmaceutically effective amount of gabapentin.

7. A method of claim 6, wherein said gabapentin is administered orally.

8. A method of claim 6, wherein said amount is from about 400 to 1,200 mg taken twice a day.

9. A method of treating a patient with symptoms of benign positional vertigo and migraine headache, comprising:

administering a pharmaceutically effective amount of a pharmaceutically acceptable salt of divalproex.

10. A method of claim 9, wherein said salt of divalproex is sodium.

11. A method of claim 9, wherein said pharmaceutically acceptable salt of divalproex is administered orally.

12. A method of claim 9, wherein said amount is from about 250 to about 1,000 mg taken twice per day.

13. A method for treating a patient with symptoms of benign positional vertigo and migraine headache, comprising:

administering a pharmaceutically effective amount of gabapentin.

14. A method of claim 13, wherein said gabapentin is administered orally.

15. A method of claim 13, wherein said amount is from about 400 to 1,200 mg taken twice a day.

16. A method of treating a patient that has vertigo when changing position in tasks selected from the group consisting of bending over standing up, extending the neck to acquire a more elevated view, getting in bed, getting out of bed, turning over in bed looking up, bending over, looking down, getting up, and lying down comprising: administering a pharmaceutically effective amount of a pharmaceutically acceptable salt of divalproex or gabapentin.

17. A method of treating a patient that experiences vertigo when changing position comprising: administering a pharmaceutically effective amount of a pharmaceutically acceptable salt of divalproex or gabapentin.

* * * * *